United States Patent
Dock, II et al.

(10) Patent No.: US 9,404,672 B2
(45) Date of Patent: Aug. 2, 2016

(54) CONCRETE CYLINDER CURING BOX AND METHOD

(75) Inventors: Marshall Dock, II, Stillwater, OK (US); Michael Fox, Nashua, NH (US); Jim O'Daniel, Stillwater, OK (US)

(73) Assignee: FLIR Commercial Systems, Inc., Goleta, CA (US)

( * ) Notice: Subject to any disclaimer, the term of this patent is extended or adjusted under 35 U.S.C. 154(b) by 346 days.

(21) Appl. No.: 13/979,034

(22) PCT Filed: Jan. 13, 2012

(86) PCT No.: PCT/US2012/021318
§ 371 (c)(1),
(2), (4) Date: Sep. 12, 2013

(87) PCT Pub. No.: WO2012/097301
PCT Pub. Date: Jul. 19, 2012

(65) Prior Publication Data
US 2013/0343734 A1 Dec. 26, 2013

Related U.S. Application Data

(60) Provisional application No. 61/432,268, filed on Jan. 13, 2011.

(51) Int. Cl.
*F24H 1/18* (2006.01)
*A47J 27/00* (2006.01)
*F24H 1/20* (2006.01)
*F24H 9/20* (2006.01)
*B28B 11/24* (2006.01)
*C04B 40/02* (2006.01)
*G01N 33/34* (2006.01)

(52) U.S. Cl.
CPC .............. *F24H 9/20* (2013.01); *B28B 11/245* (2013.01); *C04B 40/0254* (2013.01); *G01N 33/346* (2013.01); *G01N 2203/0298* (2013.01)

(58) Field of Classification Search
None
See application file for complete search history.

(56) References Cited

U.S. PATENT DOCUMENTS

| | | | |
|---|---|---|---|
| 3,769,935 A | 11/1973 | Johnson | |
| 3,947,288 A | 3/1976 | Kawano et al. | |
| 5,595,171 A | 1/1997 | Makin | |
| 6,865,515 B2 | 3/2005 | Fox et al. | |

*Primary Examiner* — Thor Campbell
(74) *Attorney, Agent, or Firm* — McAfee & Taft (57) ABSTRACT

The present disclosure describes a curing box including a circulation assembly which substantially eliminates temperature stratification of a first fluid within the box. Additionally, the curing box includes an internal temperature sensor and an external temperature sensor which provide data to a control module. The control module permits adjustment of the fluid temperature within the box. The present disclosure additionally provides a method for curing a specimen in the curing box. The method compares the temperature signal from the external sensor to the internal sensor and adjusts the temperature of the fluid in the box to match the temperature reported by the external sensor. Additionally, the method controls the flow of a second fluid into the box thereby circulating the first fluid to substantially eliminate temperature stratification of the first fluid in the box. Thus, the method provides a controlled environment for curing the specimen.

19 Claims, 10 Drawing Sheets

CONCRETE CYLINDER CURING BOX AND METHOD

CROSS-REFERENCE TO RELATED APPLICATIONS

This application claims priority to U.S. Provisional Application Ser. No. 61/432,268, filed on Jan. 13, 2011, and incorporated herein by reference.

FIELD OF DISCLOSURE

The inventive concept(s) disclosed herein generally relates to concrete curing boxes, and more particularly, but not by way of limitation to a wet concrete curing box for curing concrete test specimens with a built-in temperature control system.

BACKGROUND

It is standard practice in the construction industry to test samples of various materials used during construction. This is especially true of concrete, where many field cured specimens are generally required when structural concrete is poured. These specimens are taken from a number of locations across the element or slab when it is poured, and are typically formed as concrete test cylinders.

The American Society for Testing and Materials (ASTM), the American Concrete Institute (ACI), and the American Association of State Highways and Transportation Officials (AASHTO) have developed certain criteria for the formation and testing of concrete test specimens. For examples of such standards see ASTM C 31/C 31M, ACI-301, ACI-318, ASTM C94, and AASHTO T-23. Any deviation from standard testing procedures is grounds for invalidating the obtained test results. Local and national governmental bodies have likewise adopted certain standards for concrete acceptance testing.

One important concrete acceptance testing criteria is that the field cured test specimens represent accurate samples of the cured concrete slab. Concrete curing is an exothermic process (gives off heat) due to the heat released by a hydration reaction which occurs. The build-up of too much heat or the lowering of the temperature beyond proper curing levels can result in concrete strength reduction, cracking, and/or other structural defects. Therefore, the temperature at which the test cylinders are cured is important for the proper testing of concrete. For example, the current ASTM C31/C31M standard specifies a constant curing temperature of 73° Fahrenheit, with a tolerance of ±3° Fahrenheit.

Accordingly, ASTM standards require that field cured concrete specimens, which are cast separately from the concrete slab, be treated during curing to closely approximate the heat developed during the curing process in the more massive concrete slab. If the concrete specimens are not in situ, this is difficult to achieve. Also, the specimens are kept moist until the cure is complete, just as in the case of the poured slab. Any significant variation in the procedure can result in the specimens being an inaccurate representation of the actual qualities of the cast slab they are supposed to represent.

Recently, wet concrete curing boxes have been used to provide stable environments for the curing of concrete test cylinders in situ in order to comply with ASTM standards. The existing curing boxes generally are insulated boxes which have temperature control systems installed in order to heat or cool the inside of the box as needed. The boxes also have a rack to support the test cylinders, which is typically made by bending a sheet of 14 gauge steel into a "U" shape to form the rack, and then forming holes into the top of the rack to allow for water circulation. The rack rests on corner supports extending from the bottom of the prior art curing boxes, and supports the concrete test cylinders submerged under water.

Another recent technological development has introduced the use of "loggers" disposed in the concrete slabs. See, for example, U.S. Pat. No. 6,865,515, the entire contents of which are hereby expressly incorporated herein by reference.

Some prior art wet concrete curing boxes use water pumps having an impeller within a housing above the rack for mixing the water above the rack during the curing process. However, cement dust and other abrasive particles inside the box tend to reduce the service life of the water pumps, which typically results in increased expense and/or delays. Further, curing typically takes about twenty-eight days, which can increase the chance of failure of such prior art water pumps. Additionally, the rack can form a convective barrier which may cause a temperature stratification within the water.

Accordingly, a need exists for a curing box capable of providing reliable in situ concrete test specimens. It is to such a concrete cylinder curing box that the inventive concept(s) disclosed herein is directed.

SUMMARY

The present disclosure provides a curing box for curing a specimen. In a first embodiment, the curing box includes a box containing a liquid and having a fluid conduit positioned therein. The fluid conduit is in fluid communication with the exterior of the box. The fluid conduit carries a plurality of emitters that provide fluid communication between the fluid conduit and the interior of the box. Further, the curing box includes a fluid source in fluid communication with the fluid conduit. The fluid source is configured to provide a volume of fluid under pressure to the fluid conduit.

In another embodiment, the curing box previously described in the first embodiment additionally includes a heating element, a cooling element, a first sensor, a second sensor, and a control module. The heating and the cooling element adjust the temperature of the liquid in the box. The first sensor monitors the temperature of the liquid in the box. The second sensor is positioned in an external location from the box for monitoring a second temperature of the external location. The control module receives and records the temperature from the first sensor and receives and records the second temperature from the second sensor. Further, the control module controls the activation and deactivation of the cooling element, and the activation and deactivation of the heating element to thereby adjust the temperature of the liquid to substantially correspond to the second temperature.

In yet another embodiment, the curing box previously described in the first embodiment additionally includes a heating element, a cooling element, a first sensor, a user input device, and a control module. The heating and the cooling element adjust the temperature of the liquid in the box. The first sensor monitors the temperature of the liquid in the box. The control module receives and records the temperature from the first sensor and receives and records a preset temperature from the user input device. Further, the control module controls the activation and deactivation of the cooling element, and the activation and deactivation of the heating element to thereby adjust the temperature of the liquid to substantially correspond to the preset temperature.

Further, the present disclosure provides a method for curing a specimen. The method requires immersion of the specimen in a first fluid in a curing box. In one embodiment, the method utilizes a preset temperature for the first fluid in the curing box and monitors the temperature of the first fluid. To maintain the first fluid at the preset temperature, the method provides for heating or cooling the first fluid in the curing box to adjust the first fluid temperature to substantially correspond to the preset temperature. The method also provides a second fluid to the curing box and distributes the second fluid through a fluid conduit in the curing box. The distribution of the second fluid circulates the first fluid throughout the curing box in a manner to preclude temperature stratification in the first fluid.

In another embodiment, the method monitors the temperature of a second specimen positioned external to the curing box. Then the method adjusts the temperature of the first fluid in response to the monitored temperature of the second specimen. Typically, the adjustment of the temperature of the first fluid produces a temperature substantially similar to that of the second specimen.

BRIEF DESCRIPTION OF THE DRAWINGS

Like reference numerals in the FIGS. represent and refer to the same element or function. Implementations of the disclosure may be better understood when consideration is given to the following detailed description thereof. Such description makes reference to the annexed pictorial illustrations, schematics, graphs, drawings, and appendices. In the drawings:

FIG. 8 is an exploded view of an embodiment of a concrete curing box constructed according to the present disclosure.

FIG. 9 is a block diagram of an embodiment of a control module according to the present disclosure.

DETAILED DESCRIPTION

Before explaining at least one embodiment of the inventive concept(s) disclosed herein in detail, it is to be understood that the inventive concept(s) is not limited in its application to the details of construction and the arrangement of the components or steps or methodologies set forth in the following description or illustrated in the drawings. The inventive concept(s) disclosed herein is capable of other embodiments or of being practiced or carried out in various ways. Also, it is to be understood that the phraseology and terminology employed herein is for the purpose of description and should not be regarded as limiting.

In the following detailed description of embodiments of the disclosure, numerous specific details are set forth in order to provide a more thorough understanding of the inventive concept(s) disclosed herein. However, it will be apparent to one of ordinary skill in the art that the inventive concept(s) within the disclosure may be practiced without these specific details. In other instances, well-known features have not been described in detail to avoid unnecessarily complicating the description. The following detailed description refers to the accompanying drawings. The same reference numbers in different drawings may identify the same or similar elements.

The inventive concept(s) disclosed herein generally relates to concrete curing boxes, and more particularly, but not by way of limitation to a concrete curing box for concrete test cylinders with built in temperature control system and a water circulation system.

1. Description of the State of the Prior Art

Figure 1:
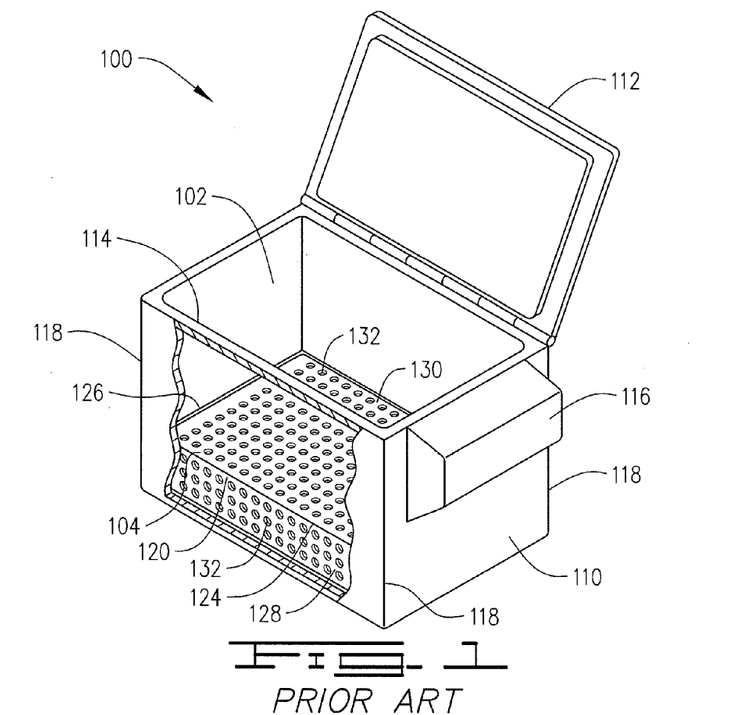
FIG. 1 is a partial cutout perspective view of a prior art concrete curing box.
Figure 2:
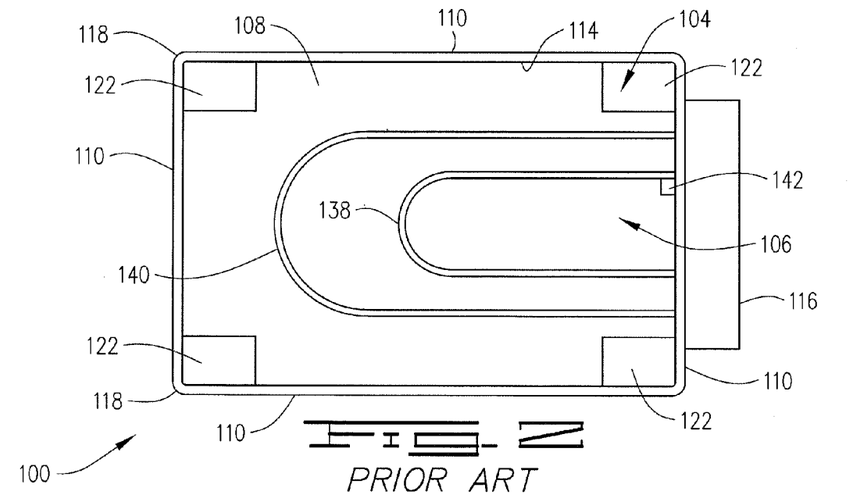
FIG. 2 is a top view of a prior art concrete curing box with the lid and rack omitted for clarity.

An exemplary prior art concrete curing box is shown in FIGS. 1-2. Therein, prior art curing box 100 comprises an insulated box 102, a support rack assembly 104, and a temperature control system 106.

The insulated box 102 comprises a bottom 108, walls 110, and a lid 112, cooperating to define a substantially rectangular enclosure 114. The enclosure 114 can be watertight. Further, the box 102 may have a control panel assembly 116 attached to the outside of one of the walls 110.

The bottom 108 is preferably substantially rectangular. Alternatively a drainage aperture may be located in one or more of the walls 110.

The walls 110 extend substantially vertically from the bottom 108 and are perpendicular to one another and connect at corners 118.

The support rack assembly 104 comprises a rack 120 and four rack supports 122. The four rack supports 122 extend from the bottom 108 and are each connected to two walls 110 at corners 118. The four rack supports 122 extend a distance above the bottom 108, such that the rack 120 is supported at a distance from the bottom 108.

The rack 120 is U-shaped and sized to fit inside the enclosure 114. The rack 120 has two long sides 124 and two short sides 126. The rack 120 has two legs 128 extending from its long sides 124 adapted to be placed upon two of the four rack supports 122 each, such that the rack 120 is supported at a distance from the bottom 108. The rack 120 functions to support the substantial weight of several concrete test cylinders (not shown). The rack 120 is made from a sheet of 14-gauge stainless steel which is bent to a U-shaped configuration to form the two legs 128. Apertures 132 are then formed into a flat surface 130 in order to allow water passage therethrough. The rack 120 is sized to fit inside the enclosure 114, such that when weight is placed upon the rack 120 it is supported by the legs 128 to prevent buckling of the rack 120. The rack 120 separates the enclosure 114 into an upper portion and a lower portion which are in fluid communication with one another via its apertures 132.

Referring now to FIG. 2, the temperature control system 106 comprises a heating element 138, a cooling element 140, and a temperature sensor 142. The temperature control system 106 also has a control module (not shown) disposed inside the control panel assembly 116 of the box 102. The heating element 138, the cooling element 140, and the temperature sensor 142 are disposed inside the lower portion of the enclosure 114 and extend parallel to the legs 128 of the rack 120. The control module regulates the temperature inside the enclosure 114 by selectively activating the heating element 138 and/or the cooling element 140 in response to data received from the temperature sensor 142, in order to maintain a pre-set temperature inside the enclosure 114.

2. Detailed Description of the Inventive Concept(s)

Figure 3:
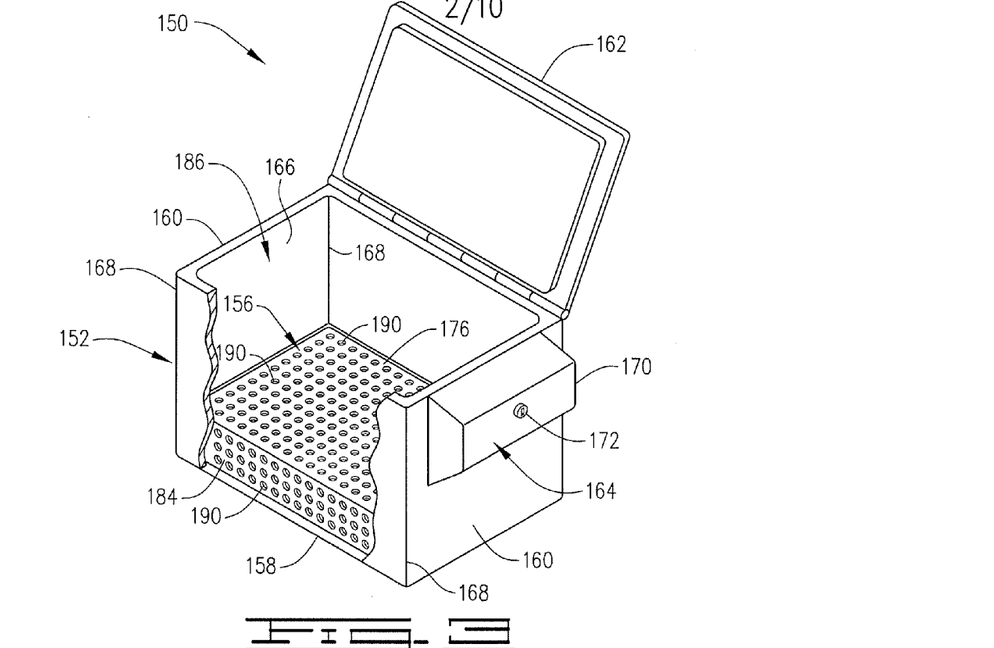
FIG. 3 is a perspective partial cutout view of an embodiment of a concrete curing box constructed according to the present disclosure.
Figure 4:
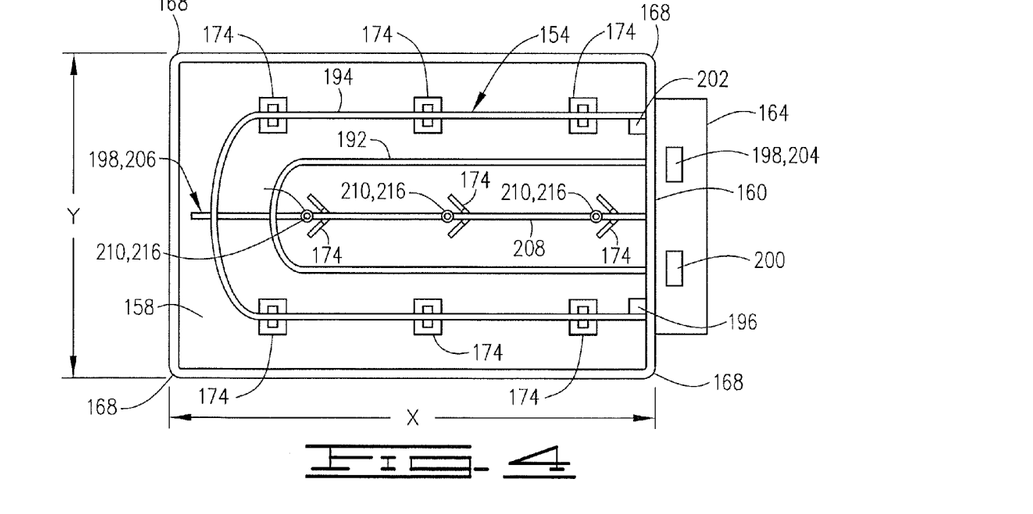
FIG. 4 is a top view of an embodiment of the concrete curing box shown in FIG. 3 with the rack omitted for clarity.

Referring now to FIGS. 3-4, shown therein is an example of a curing box 150 constructed in accordance with the present disclosure. Generally the curing box 150 comprises a box assembly 152, a temperature control assembly 154, and a rack assembly 156.

The box assembly 152 has a bottom 158, walls 160, a lid 162, and a control module housing 164.

The bottom 158, walls 160, and lid 162 cooperate to form a cavity 166, which can be substantially watertight. The cavity 166 has a length x and a width y. The bottom 158 is preferably substantially rectangular in shape. The walls 160 may have one or more closeable drainage apertures (not shown) formed therein in order to selectively drain the water from the curing box 150 for easier transportation and/or storage. The bottom 158 may have one or more insulating layers therein and can be made of any non-corrosive material having sufficient strength and durability such as plastic for example. One or more optional casters (not shown) may be attached to the bottom 158 in order to allow the curing box 150 to be wheeled to a desired location. It is to be understood that the bottom 158 may have other suitable shapes and geometries as will become apparent to a person of ordinary skill in the art in light of the present disclosure.

The walls 160 preferably extend substantially vertically from the bottom 158, and are preferably substantially perpendicular to one another and connect to one another at corners 168. The walls 160 can be made of any suitable non-corrosive material having sufficient strength and durability such as plastic for example, and may have one or more insulating layers therein. It is to be understood that while four walls 160 are shown, the curing box 150 according to the inventive concept(s) disclosed herein can have any number of walls 160, can be of any suitable size, and may have geometries other than substantially rectangular. Further, the walls 160 can be constructed from an opaque material to shield the cavity 166 from direct sunlight and, if used, radiant heating devices.

The lid 162 is preferably substantially rectangular in shape and is sized to span the distance between the walls 160. The lid 162 can be removably positioned on top of walls 160. The lid 162 may alternatively be pivotably or slidably connected to one or more of the walls 160, such that it can be selectively opened and closed. The lid 162 can be made of any suitable non-corrosive material having sufficient strength and durability such as plastic for example, and may have one or more insulating layers built therein. The lid 162 can have an optional latch (not shown) which may be lockable to prevent tampering as well as an optional seal to reduce evaporation, but which is preferably not airtight to allow venting. Additionally, the lid 162 can be attached to one or more of the walls 160 by any other suitable means such as slides as will become apparent to a person of ordinary skill in the art in light of the present disclosure.

The control module housing 164 preferably comprises a box 170, which is preferably attached to one of the walls 160 and may be disposed outside of the cavity 166. The control module housing 164 functions to house components of the temperature control assembly 154 as will be discussed below. The control module housing 164 may also house any other components of the curing box 150 that are kept outside of the cavity 166 but should be protected from the environment. The control module housing 164 can be made of any suitable non-corrosive material such as plastic or galvanized steel for example, and may optionally be water and/or airtight. The control module housing 164 protects its contents from the environment and may have an optional latch 172, which may be lockable to prevent tampering. The control module housing 164 may also have a transparent portion (not shown) such that readouts from a control module display (not shown) can be observed without opening the control module housing 164. Additionally, the control module housing 164 may define one or more ports (not shown) in the surface thereof. Such ports can function to allow a power cord (not shown) to enter the control module housing 164, or to allow other wired connections such as for example Ethernet cables, coaxial cables, or USB-cables. At least a portion of the control module housing 164 may optionally be permeable to wireless signals, to allow wireless communication with temperature control assembly 154.

Referring now to FIGS. 3-7C, the rack assembly 156 comprises a plurality of support members 174 and a rack 176.

Figure 5:
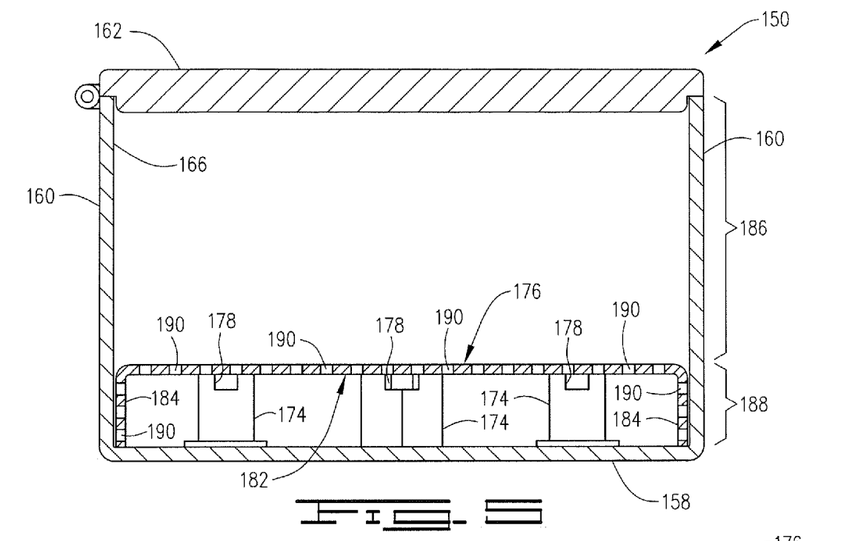
FIG. 5 is an end view of an embodiment of a concrete curing box according to the present disclosure with the temperature control assembly omitted for clarity.
Figure 6:
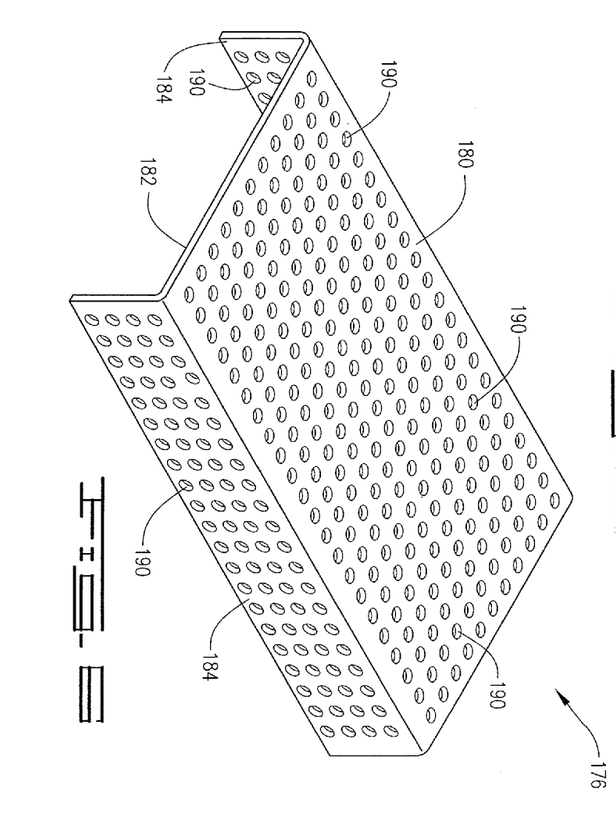
FIG. 6 is a perspective view of an embodiment of a rack constructed according to the present disclosure.

The plurality of support members 174 extend substantially vertically from the bottom 158. Referring now to FIGS. 4-5, the plurality of support members 174 are shown as being disposed symmetrically about the bottom 158. The plurality of support members 174 have one or more notches 178 formed therein to allow the passage of one or more heating element 192, one or more cooling element 194, and one or more fluid conduit 208 therethrough.

Figure 7A:
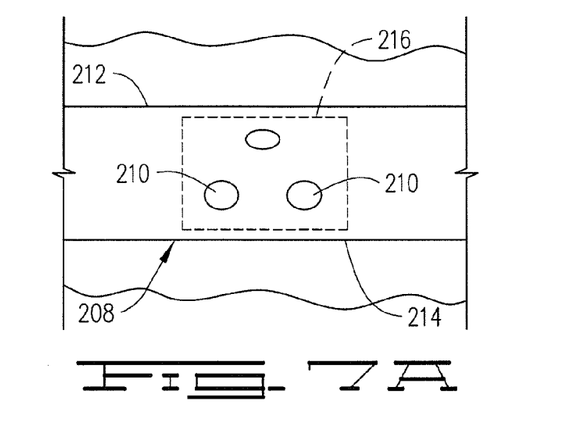
FIG. 7A is a bottom sectional view of an embodiment of a fluid conduit according to the present disclosure.
Figure 7B:
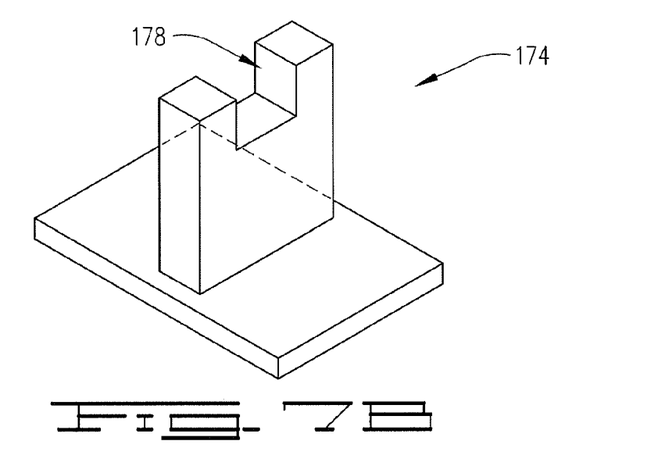
FIG. 7B is a perspective view of an embodiment of a rack support member according to the present disclosure.

An exemplary embodiment of the plurality of support members 174 is shown in FIG. 7B as being T-shaped. The horizontal arm of the "T" is disposed on the bottom 158 of the box 150, and the vertical arm of the "T" extends vertically therefrom and has the notch 178 formed therein and adapted to receive one or more of the heating element 192, the cooling element 194, and the fluid conduit 208.

Figure 7C:
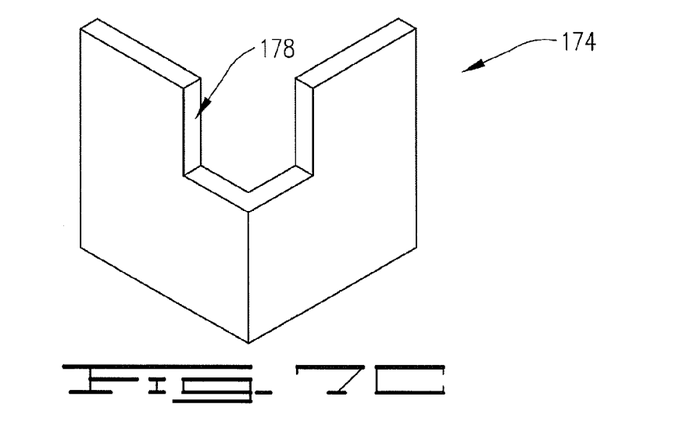
FIG. 7C is a perspective view of an alternative embodiment of a rack support member according to the present disclosure.

Another embodiment of the plurality of support members 174 is shown in FIG. 7C as being "V"-shaped. The "V" shape is positioned such that the arms of the "V" extend vertically from the bottom 158 of the box 150, and the one or more notch 178 preferably formed into the point of the "V" allows the passage of one or more of the heating element 192, the cooling element 194, and the fluid conduit 208 therethrough.

The plurality of support members 174 are shown as T-shaped and/or V-shaped support members 174, but it is to be understood that any suitable shapes can be used for the support members 174, such as square, triangular, cylindrical, star-shaped, or elliptical for example. The plurality of support members 174 function to partially support the weight of the rack 176 and one or more concrete test specimens. The plurality of support members 174 can also function to suspend the temperature control assembly 154 a distance above the bottom 158 such that the components of the temperature control assembly 154 are held in a concentric coplanar orientation by the plurality of support members 174. It is to be understood that while the plurality of support members 174 and the bottom 158 are shown as separate components, the plurality of support members 174 and the bottom 158 can alternatively be formed as a unitary structure. For example, one of the support members 174 can be a long piece of angle iron extending along the length and down the middle of the rack 176 that is perforated to allow for fluid circulation.

In general, the rack 176 is optional and may be eliminated if the temperature control assembly 154 is built into the bottom 158 and/or the walls 160 of the box 150. The rack 176 can have a top surface 180, a bottom surface 182, and legs 184 extending substantially perpendicularly (e.g. between about 85-95 degrees) below the bottom surface 182. The legs 184 may rest on the bottom 158 and can at least partially support the weight of the rack 176 and the concrete test cylinders (not shown) placed thereon. The legs 184 and the rack 176 can for example be formed by bending a single sheet of non-corrosive perforated rigid material such as stainless steel, or the legs 184 can be attached to the rack 176 by any suitable means such as welds, brackets, flanges, bolts, rivets, and adhesives for example. The bottom surface 182 can rest on one or more of the plurality of support members 174, such that the rack 176 is at least partially supported by one or more of the plurality of support members 174. While two legs 184 are shown in the FIGS., it is to be understood that varying numbers of legs 184 are contemplated for use with the inventive concept(s) disclosed herein, which legs 184 can have varying orientations and configurations. When the rack 176 is placed inside the box 150, the rack 176 separates the box 150 into an upper portion 186 (see FIG. 5) and a lower portion 188 (see FIG. 5). The rack 176 can be made of a sheet of stainless steel having a gauge of less than 14 such as 16 gauge so that the rack 176 is less costly than the prior art rack 120. The rack 176 can have a plurality of apertures 190 formed in the top surface 180 and/or the legs 184 thereof. The apertures 190 can have varying shapes and sizes and function to provide fluid communication pathways between the lower portion 188 and the upper portion 186 of the box 150. The apertures 190 can be formed into the top surface 180 and/or legs 184 prior to forming the legs 184, or alternatively after forming the legs 184. Because the weight of the concrete cylinders is supported by the legs 184 and the plurality of support members 174, the apertures 190 can comprise more than 50% of the surface of the rack 176, such as for example between 50-70% to increase the amount of water circulation between the upper portion 186 and the lower portion 188 while still maintaining sufficient strength to support the test specimens. It has been found that when the rack 176 is constructed of perforated 14 gauge stainless steel, a suitable ratio of collective area for apertures/total surface area is 60%. However, this can be varied depending upon the type of material being used to form the rack 176. For example, the ratio can be increased by using a smaller gauge (e.g., 12 gauge) of stainless steel.

The temperature control assembly 154 preferably comprises the heating element 192, the cooling element 194, a temperature sensor 196, a circulator assembly 198, a control module 200, and a logger 202.

The heating element 192 can be disposed in a lower portion 188 of the box 150 and is shown as a U-shaped tubular element extending inwardly from one of the walls 160 and disposed substantially parallel to the bottom 158. The heating element 192 can be sized such that it spans more than 50% of the length x of the box 150. In the embodiment shown, the heating element 192 is not supported by any of the support members 174; however, if additional support for the rack 176 is desired, then the heating element 192 can pass through the notches 178 within the support members 174. In this embodiment, the support members 174 should be constructed of a material that will not be melted by the heating element 192. The material can be a metal, such as stainless steel and/or a plastic having a melting point above a maximum temperature achieved by the heating element 192. The heating element 192 can be any heating element known in the art such as a resistive heating element, Peltier-type heating element, a heat pump, and/or a heat exchanger for example. It is to be understood that while the heating element 192 is shown as a U-shaped element, suitable heating elements having varying shapes, sizes, and orientations can be used within the scope of the inventive concept(s) disclosed herein as will be apparent to a person of ordinary skill in the art in light of the present disclosure. Additionally, two or more heating elements 192 can be used rather than one heating element 192. In an embodiment where the heating element comprises a Peltier heating element or a thermoelectric heat pump, the cooling element 194 may be omitted due to the ability of each device to both heat and cool.

The cooling element 194 can be disposed in the lower portion 188 of the box 150 and is shown as a U-shaped element extending inwardly from one of the walls 160 and disposed substantially parallel to the bottom 158. The cooling element 194 can be sized such that it extends past 50% of the length x of the cavity 166. The cooling element 194 preferably passes through one or more of the notches 178 formed in the plurality of support members 174 and is supported at a distance from the bottom 158 by one or more of the plurality of support members 174. The cooling element 194 can be a U-shaped loop and can be sized to be smaller than the heating element 192, such that the heating element 192 and the cooling element 194 are arranged in a coplanar concentric configuration. While the cooling element 194 is shown as a U-shaped element it is to be understood that cooling elements having varying shapes, sizes, and configurations can be used within the scope of the inventive concept(s) disclosed herein, as long as such cooling elements 194 function to dissipate heat from the box 150. The cooling element 194 can be a Peltier-type cooling element, a heat sink, a heat pump, a heat exchanger, or can alternatively be a thermally-conductive conduit through which a refrigerant such as a refrigerant of the type R134a is circulated via a vapor-compression refrigeration system. Other suitable refrigerants, such as cool air, cold water, carbon dioxide ($CO_2$), chlorofluorocarbon (CFC) and/or hydrofluorocarbon (HFC) based compounds, ammonia, and nitrogen, for example, can alternatively be used with the inventive concept(s) disclosed herein. In one embodiment where a Peltier-type cooling element is used, the heating element 192 may be omitted due to the ability of the Peltier-type cooling element to both heat and cool in a single device.

The temperature sensor 196 is in thermal communication with the cavity 166 of the box 150, such that the temperature sensor 196 is capable of measuring the temperature of the fluid inside the box 150 while the concrete test specimens are curing. The temperature sensor 196 can be partially or completely disposed inside the box 150 and is configured to communicate the measured data to the control module 200. The temperature sensor 196 can be any temperature sensor known in the art such as a thermocouple or a thermistor for example. It is to be understood that more than one temperature sensor 196 can be used, and if two or more temperature sensors 196 are used they may be vertically and/or horizontally offset inside the cavity 166 of the box 150. For example, one or more temperature sensors 196 may be disposed inside a lower portion 188, and one or more temperature sensors 196 may be disposed in an upper portion 186 of the box 150.

The circulator assembly 198 is adapted to circulate the fluid inside the box 150 to help provide a homogenous temperature distribution within the fluid. Preferably, the circulator assembly 198 circulates the fluid inside the box 150 without an impeller within a housing engaging the fluid surrounding the concrete test specimens, which improves the reliability of the circulator assembly 198 over prior art circulator assemblies. In one embodiment, the circulator assembly 198 comprises a fluid source 204, and a fluid distribution assembly 206 positioned underneath the rack 176 to form bubbles which move the fluid through the rack 176 to circulate the fluid inside the box 150. The rack 176 may form a convective barrier that causes stratification of the fluid within the cavity 166. Preferably, the fluid distribution assembly 206 is positioned underneath the rack 176 and designed to force or move the fluid through the rack 176 to destratify the fluid. The fluid distribution assembly 206 can be implemented in other ways, such as a pump or an acoustic driver (not shown) providing electrically alternating current signals to one or more speaker (not shown) and/or solenoid (not shown) positioned in the bottom 158 and/or the walls 160 to introduce acoustic and/or pressure waves into the fluid. Alternatively, the fluid distribution assembly 206 can be positioned above the rack 176 to force fluid above the rack 176 to be underneath the rack 176 to reduce any stratification caused by the rack 176. For example, the fluid distribution assembly 206 can include one or more pumps having inlet(s) positioned to receive fluid above the rack 176 and outlet(s) positioned to direct fluid underneath the rack 176.

The fluid source 204 can circulate air or a gas within the fluid inside the box 150 to stir or mix the fluid. For example, the fluid source 204 can be an air pump capable of providing a certain volume of a gas or a liquid at a certain pressure which volume and pressure may vary according to the box 150 sizes and configurations. The fluid source 204 may have varying input capabilities in which case the fluid source may be controlled by the control module 200. The fluid source 204 can be at least partially housed inside the control module housing 164, housed in a separate housing (not shown) and/or housed inside the box 150. The fluid source 204 is preferably positioned above the level of the liquid inside the box 150 in order to prevent backflow of liquid into the fluid source 204 when the fluid source 204 is not operating, or in case of a power failure. Alternatively, one or more one-way valves (not shown) can be used to prevent the backflow of liquid into the fluid source 204. The air or gas that the fluid source 204 circulates within the fluid inside the box 150 can come from a variety of sources, such as ambient air, a compressed gas container, or the inside of the box 150 for example. When the air or gas circulated by the fluid source 204 comes from inside the box 150, such air or gas may be obtained by a conduit (not shown) in fluid communication with the inside of the box 150 and the fluid source 204, and installed such that it extends above the expected maximum level of the liquid inside the box 150. This configuration would allow for the pressure inside the box 150 to remain substantially unchanged by the operation of the fluid source 204 as any air or gas that is be circulated within the fluid inside the box 150 would be withdrawn from the inside of the box 150 above the level of the fluid. The fluid source 204 is in fluid communication with the fluid distribution assembly 206 as will be described below.

The fluid distribution assembly 206 is immersed within the fluid inside the box 150 so that the air or gas provided by the fluid source 204 escapes from the fluid distribution assembly 206 to form bubbles in the fluid and thereby mix the fluid in the box 150. The fluid distribution assembly 206 preferably comprises a fluid conduit 208, and emitters 210.

The fluid conduit 208 is disposed in the lower portion 188 of the cavity 166 and preferably extends substantially perpendicularly from the wall 160 adjacent to the control module 200. The fluid conduit 208 can be attached to the wall 160, or may extend through an aperture (not shown) formed into the wall 160. The fluid conduit 208 is shown as a straight conduit extending over the center line of the bottom 158, and sized to span about 90% of the length x of the cavity 166. The fluid conduit 208 may extend substantially parallel to the bottom 158, and can pass through one or more of the notches 178 formed in the plurality of support members 174. The fluid conduit 208 may also be parallel to and disposed in a coplanar orientation relative to the heating element 192 and the cooling element 194. The fluid conduit 208 has an open end to receive the air or gas, a closed end, a top surface 212 and a bottom surface 214 (FIG. 7A).

Referring now to FIG. 7A, the emitters 210 are preferably disposed along the bottom surface 214 of the fluid conduit 208 so that bubbles emitted by the emitters 210 clean the fluid conduit 208 while also helping it prevent debris from entering or interfering with the emitters 210. Three emitters 210 are shown in a group 216, such that the emitters 210 are vertically and laterally offset from one another along the bottom surface 214 of the fluid conduit 208 although the number of emitters 210 in each group 216 may be more or less than three. Also, the relative positions of the emitters 210 can be changed. The emitters 210 are in fluid communication with the fluid conduit 208 and with the cavity 166. Each group 216 can have one, two, three, or more emitters 210 disposed along the bottom surface 214 and/or other location on the fluid conduit 208, such as the top surface 212, and/or the side of the fluid conduit. The emitters 210 and the groups 216 are preferably positioned to cause mixing along the length and the width of box 150. One arrangement that has been found especially desirable is to provide three groups 216 with one group 216 positioned substantially centrally on the fluid conduit 208, and the other two groups 216 symmetrically offset therefrom along the fluid conduit 208 and positioned within a distance of about 25% of the length x of the box 150 from the walls 160 as shown in FIG. 4. It is to be understood that other arrangements for the emitters 210 may also be used. The emitters 210 can have varying shapes and sizes, can be grouped in groups of varying numbers, or ungrouped. It is to be also understood that emitters 210 can be disposed in varying directions and at varying positions along the fluid conduit 208. An alternative embodiment (not shown) may have more than one fluid conduit 208, and/or may have only a single emitter 210. In another embodiment, the emitters 210 may comprise one or more air stones (not shown) or one or more nozzles (not shown). The gas and/or air may be heated or cooled as needed to substantially correspond to the temperature inside the box 150 prior to being introduced inside the box 150. For example, the fluid source 204 can have an intake positioned inside the box 150 to receive gas and/or air from within the box 150, but above the expected level of fluid within the box 150, such that the air and/or gas is recirculated within the box 150. Alternatively, the fluid source 204 can have an intake positioned outside of the box 150 to draw ambient air into the box 150. In one embodiment, the walls 160 of the box 150 have a height and the intake is positioned above three-quarters of the height of the walls 160 to be above the expected level of fluid within the box 150. It is to be understood that gasses other than air and/or liquids other than water are contemplated for use with the inventive concept(s) disclosed herein.

An exemplary embodiment of a control module 200 according to the inventive concept(s) disclosed herein is shown in FIG. 9. The control module 200 is adapted to control the heating element 192, the cooling element 194, and the circulator assembly 198. The control module 200 is further adapted to receive and/or record data from the temperature sensor 196 and/or from the logger 202, and/or from a match temperature sensor 217 (not shown). The control module 200 is at least partially housed inside the control module housing 164. The control module 200 can have one or more processors 218, one or more output devices 220, one or more input devices 222, and one or more memory devices 224. The one or more processors 218 may be any processor known in the art such as one or more of: a Central Processing Unit (CPU), a microprocessor, a Field Programmable Gate Array (FGPA), or the like, or combinations thereof, for example. The one or more processors may function to control the operation of the temperature control assembly 154 and/or the circulator assembly 198 as will be described below. The one or more memory devices 224 can be a hard drive, a solid state drive, Random Access Memory (RAM), a flash memory, a floppy drive, or an Electronically Erasable Programmable Read-only Memory (EEPROM), or combinations thereof, for example. The one or more memory devices 224 can include a first memory device 224a and a second memory device 224b. The second memory device 224b can be a removable memory device such that the second memory device 224b can be sent off-site to a quality control lab, for example, such that the quality control lab can access and verify data contained in the second memory device 224b. The one or more memory devices 224 can store computer executable code and/or other data. The computer executable code stored in the one or more memory devices 224 can be accessed by the one or more processor 218 to obtain the data stored therein in situ, or over a network such as a Local Area Network (LAN), wireless network, or the Internet. Data contained in the one or more memory devices 224 may also be remotely accessible over a network such as LAN, a cellular phone network, a Wi-Fi network, or the Internet, for example, by using a transceiver 226. The control module 200 can monitor the temperature inside the box 150 via the temperature sensor 196 in real time and adjust the heating element 192 and/or the cooling element 194 accordingly via a heating element system 227 and/or a cooling element system 228. The heating element system 227 can be provided with relays, circuitry and/or controllers to adjust the heat being generated and/or absorbed by the heating element 192. The cooling element system 228 can function based upon the principles of absorption, heat pump cycles, or refrigeration cycles, and may include components such as one or more compressor, heat pump, condenser, expansion valve, evaporator, controller and/or other devices and/or circuitry working together to adjust the heat absorption of the cooling element 194.

If the temperature inside the box 150 is higher than the preset temperature, the control module 200 can deactivate the heating element 192 and/or activate the cooling element 194. If the temperature inside the box 150 is lower than the preset temperature, the control module 200 can deactivate the cooling element 194 and/or activate the heating element 192. If the temperature inside the box 150 is equal to the preset temperature, or falls within an acceptable tolerance window, the control module 200 can deactivate both the cooling element 194 and the heating element 192. The control module 200 can operate the circulator assembly 198 continuously or intermittingly throughout the curing process. Alternatively, the circulator assembly 198 may be controlled and operated by a separate control module (not shown) such as an on/off switch for example.

The output device 220 can be a Light Emitting Diode display (LED), a Liquid Crystal Display (LCD), a touch-screen display, an analog temperature gauge, or a digital temperature gauge, for example. The control module 200 can produce audible and/or visible alert signals when the temperature inside the box 150 varies from a pre-set value and/or tolerance, such as 73° F.±3° F., for example. The alert signal can be displayed such that it is visible to a worker observing the box 150, or can be transmitted to a location remote from the box 150 to an onsite construction office, or to an off-site control center. A user may manually adjust the temperature inside the box 150 via the input device 222, or pre-set a temperature to be automatically maintained by the control module 200 inside the box 150. The processor 218 may also execute instructions to enable a user to adjust and/or monitor the temperature inside the box 150 remotely over a network such as a wireless network, a LAN, a telephone network, the Internet, and/or a cellular network. For example, the processor 218 can be programmed to host a web-site having a Uniform Resource Locator and/or an IP address accessible via the Internet to permit the user to adjust and/or monitor the temperature. Further, the processor 218 may receive a temperature log from an in-situ specimen and/or the input device 222 and/or a remote network and control the temperature inside the box 150 to substantially correspond to the temperature log.

The control module 200 can be powered by any suitable power source, such as one or more of: a conventional/rechargeable battery, a car battery, a solar cell, a portable generator, and/or by the electrical grid. Power source redundancy can be assured, for example, by having a primary power source and one or more backup power sources to endure power throughout the curing process. The control module 200 can preferably encrypt data before recording and/or transmitting it to ensure data integrity.

The control module 200 may be programmed to facilitate match curing in a new and inventive way. Match curing is a concept known in the art in which a controller is utilized to read temperatures from an in-situ curing concrete mass, such as a road, and a temperature sensor on the concrete specimen curing in a dry environment. The controller regulates a heating element connected to a metal mold of the concrete specimen so that the temperature of the concrete specimen substantially corresponds to the temperature of the in-situ curing concrete mass. In accordance with the present disclosure, the match temperature sensor (not shown) can be mounted in or on an in-situ curing concrete mass, such as a road, while one or more concrete test specimens are cured within the box 150 in a wet environment. The control module 200 is programmed and operated to cause the temperature within the fluid of the box 150 (as read by the temperature sensor 196) to substantially correspond to the temperature of the in-situ concrete mass read by the match temperature sensor (not shown). Thus, in the present disclosure, the temperature of the concrete test specimens is regulated indirectly in a wet environment via temperature readings and temperature control of the fluid in a new and inventive manner.

Figure 10A:
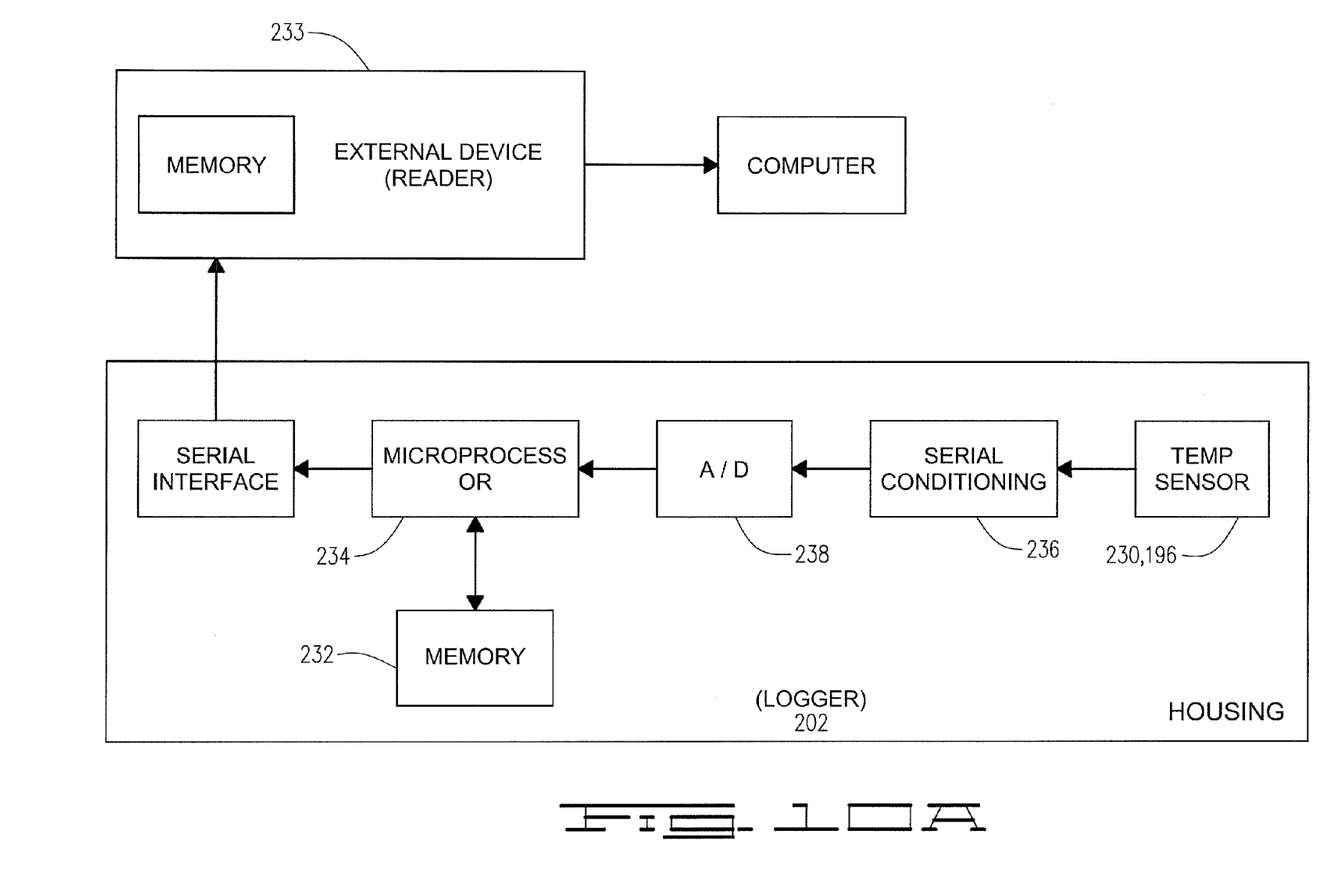
FIG. 10A is a block diagram of an embodiment of a logger according to the present disclosure.
Figure 10B:
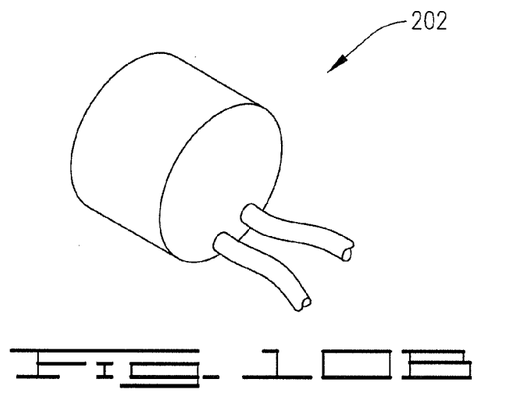
FIG. 10B is an end, perspective view of an embodiment of a logger according to the present disclosure.

Referring now to FIGS. 10A and 10B, the logger 202 can be a data logger that is adapted to record at least one data input. The logger 202 can be partially or completely housed inside the control module housing 164. The logger 202 can be adapted to log temperature and/or other data from the temperature sensor 196 and/or the logger 202 can be a totally separate from the control module 200 and/or have a temperature sensor 230 separate from the temperature sensor 196. The logger 202 can be a sensor/recorder device which monitors and logs certain variables inside the box 150, such as temperature, pH, etc. The data can be extracted from the logger 202 and used to assess the compliance of this particular process batch with applicable ASTM or other standards, or contractor requirements. In order to ensure quality control, the data recorded in the logger 202 can be encrypted and/or unalterable once recorded by the logger 202. The data can be extracted and/or transmitted to an external device 233 and sent to a remote location and decrypted/verified by an independent quality control entity and/or the project managers. Exemplary embodiments of the external device 233 are described in U.S. Pat. No. 6,865,515, which is incorporated herein by reference.

In one embodiment shown in FIG. 10B, the logger 202 may comprise a separate device, which is simply placed, lowered, or dropped inside the cavity 166 such that the logger 202 is in thermal communication with the liquid inside the box 150. In another embodiment, the logger 202 may be a separate device suspended inside the cavity 166 by use of wires, ropes, strings, or chains for example, such that the logger 202 is in thermal communication with the liquid inside the box 150.

The logger 202 can optionally save such data on a removable memory (not shown), and/or can transmit and/or receive data to the external device 233 wirelessly and/or over a network such as a LAN or the Internet via a wireless or wired transceiver. Additionally, the logger 202 may also receive and log data from thermometers and/or humidity sensors embedded in the main concrete body, and may cooperate with the control module 200 to maintain the concrete test specimens at the same temperature as the main concrete body, in order to obtain more representative test specimens. The logger 202 may be powered by one or more of: a conventional/rechargeable battery, a car battery, a solar cell, a portable generator, or by the electrical grid in order to provide for uninterrupted data logging throughout the curing process. Power supply redundancy can be built in for example by securing one primary and one or more secondary power sources for the logger 202. Examples of a suitable logger 202 are described in U.S. Pat. No. 6,865,515.

The logger 202 can include at least one temperature sensor 230, a first memory device 232, one or more processor 234, and a power source. The first memory device 232 may be one of several memory devices, such as a RAM device within a computer, flash memory, or a EEPROM. Within the logger 202, the temperature sensor 230 is connected to the processor 234 preferably by a signal conditioning circuit 236 and/or an Analog to Digital (A/D) converter 238. The temperature sensor 230 is typically a thermistor for which the electrical resistance changes in an electrical circuit based on the changes of temperature sensed. The temperature sensor 230 sends temperature dependent data signals to the processor 234 for processing. The processor 234 may be any processor known in the art, such as one or more microprocessor, a CPU, one or more FGPA, a microcontroller, and/or combinations thereof, for example. The logger 202 may be housed inside the control module housing 164, or may be housed in a separate housing (not shown). The logger 202 may be a part of the control module 200 such that the logger 202 receives data from the temperature sensor 196. Alternatively, the logger 202 may be a separate device. It is to be understood that more than one logger 202 may be used with the inventive concept(s) disclosed herein.

In operation, the curing box 150 preferably operates as follows: one or more concrete test cylinders (not shown) are placed inside the box 150 onto the rack 176. The box 150 is filled with water or another suitable liquid. The lid 162 is closed, and the control module 200 is operated to set the temperature inside the box 150. It is to be understood that the box 150 may alternatively be filled with liquid and heated/cooled to a desired pre-set temperature prior to inserting the concrete test cylinders inside the box 150. The circulator assembly 198 can be operated to circulate the liquid inside the box 150, by pumping air, or another suitable gas/liquid through the fluid conduit 208 and the emitters 210. Gas bubbles can rise upward from the lower portion 188, through the apertures 190 of the rack 176, and through the upper portion 186. The gas bubbles rising through the liquid inside the box 150 can cause the liquid to be circulated throughout the box 150. The box 150 may be locked or sealed while the concrete inside the concrete test cylinders cure, which typically takes about twenty eight days. Once the concrete has cured, the concrete test cylinders are removed from the box 150, and are sent to an off-site location for quality control and/or concrete strength testing. The data recorded by the logger 202 can also be sent to the control lab with the concrete test cylinders to establish proper on-site handling procedures.

The curing box 150 is preferably designed to meet applicable industry standards. For example, Section 929.03.6 of Rhode Island's requirements for wet concrete curing boxes lists the following requirements: approximate internal dimensions of 54 inches in length; 18 inches in width; and 17 inches in depth. The requirements specify that the box must be insulated, hinged at the back, and have a lock at the front; be leak-proof and be able to hold a pool of water at the bottom of the cavity approximately 4 inches deep. The requirements further specify a drainpipe provided through the side of the box for maintenance purposes. Suitable means of support are required to hold the concrete cylinders above the water surface. A thermometer which can be read from the outside is also required to be installed to measure the internal temperature of the box. A thermostat is required to maintain the water at a uniform temperature of 73° F.±3° F. using heating or cooling cycles throughout an ambient temperature range of −10° F. to 100° F. The requirements in Rhode Island also state that a concrete curing box of a design and manufacture different from that described above, but which possesses equal characteristics may be employed provided that it is approved in writing by an engineer in charge of the project.

As another example, the State of Georgia requires a curing box constructed of non-corroding materials and capable of storing a minimum of 22 concrete test cylinders measuring 6 inch×12 inch (150 mm×300 mm) each, to be stored vertically with the lid closed. Additionally, Georgia requires that the wet curing box meets the moisture and temperature requirements of AASHTO T-23.

As yet another example, the State of Alabama has similar test cylinder capacity requirements for wet concrete curing boxes, but further requires approval by a Materials and Tests Engineer prior to beginning any concrete placement.

It is to be understood that the above requirements are exemplary only, and are not to be construed as limitations on the size or configurations of embodiments of the inventive concept(s) disclosed herein. It is to be further understood that other public and/or private entities, as well as other national and international bodies may specify different requirements for wet concrete curing boxes, which requirements can be implemented in the curing box 150 without departing from the scope of the inventive concept(s) disclosed herein.

Figure 11:
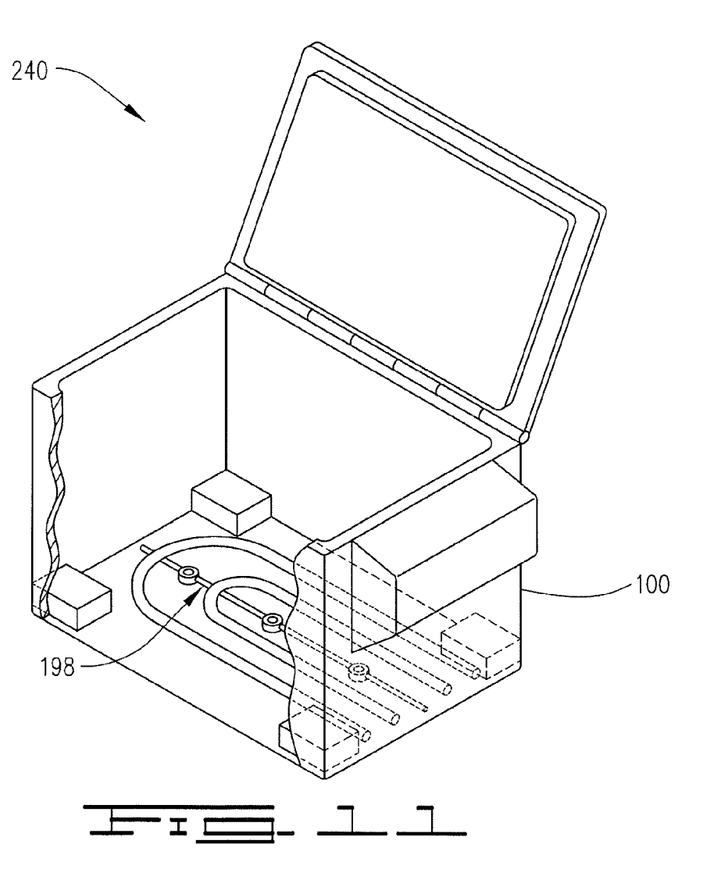
FIG. 11 is a partial cutout perspective view of a prior art curing box retrofitted with a circulator assembly according to the present disclosure, with the rack omitted for clarity.

An exemplary embodiment of a retrofitted curing box 240 having a circulator assembly 198 according to the inventive concept(s) disclosed herein is shown in FIG. 11. Generally, the retrofitted curing box 240 comprises a prior art curing box 100 which further comprises a retrofitted circulator assembly 198 as described herein above. Most existing prior art curing boxes 100 can easily be retrofitted with a circulator assembly 198 as disclosed herein with minimal investment of effort and money. The choice of an appropriate fluid source size, fluid conduit sizes, numbers and configurations, and emitter sizes, number, and configurations, will be dependent upon the size of the curing box 240 and can be determined by a person of ordinary skill in the art without undue experimentation when presented with the instant disclosure.

In order to demonstrate the reduced temperature stratification provided by the present disclosure, the temperature in a prior art curing box and a curing box constructed according to the present disclosure were equalized at 73 degrees. Ten concrete cylinder specimens were placed in each curing box along with IntelliRock™ brand loggers to monitor temperatures at the top and the bottom of each curing box, and in two specimens in each curing box. The specimens were left in each curing box for 18 hours.

After 18 hours, the digital display for each curing box indicated the internal temperature was 73 degrees. However, the actual temperature at the top of the prior art curing box was 76.5 degrees, while the actual temperature at the top of the inventive curing box was 73.2 degrees. The specimens in the prior art curing box had a temperature of 78.1 degrees with the temperature decreasing to 72.5 at the bottom of the specimens. The specimens in the inventive curing box had an even temperature from top to bottom of 74.7 degrees.

Figure 12:
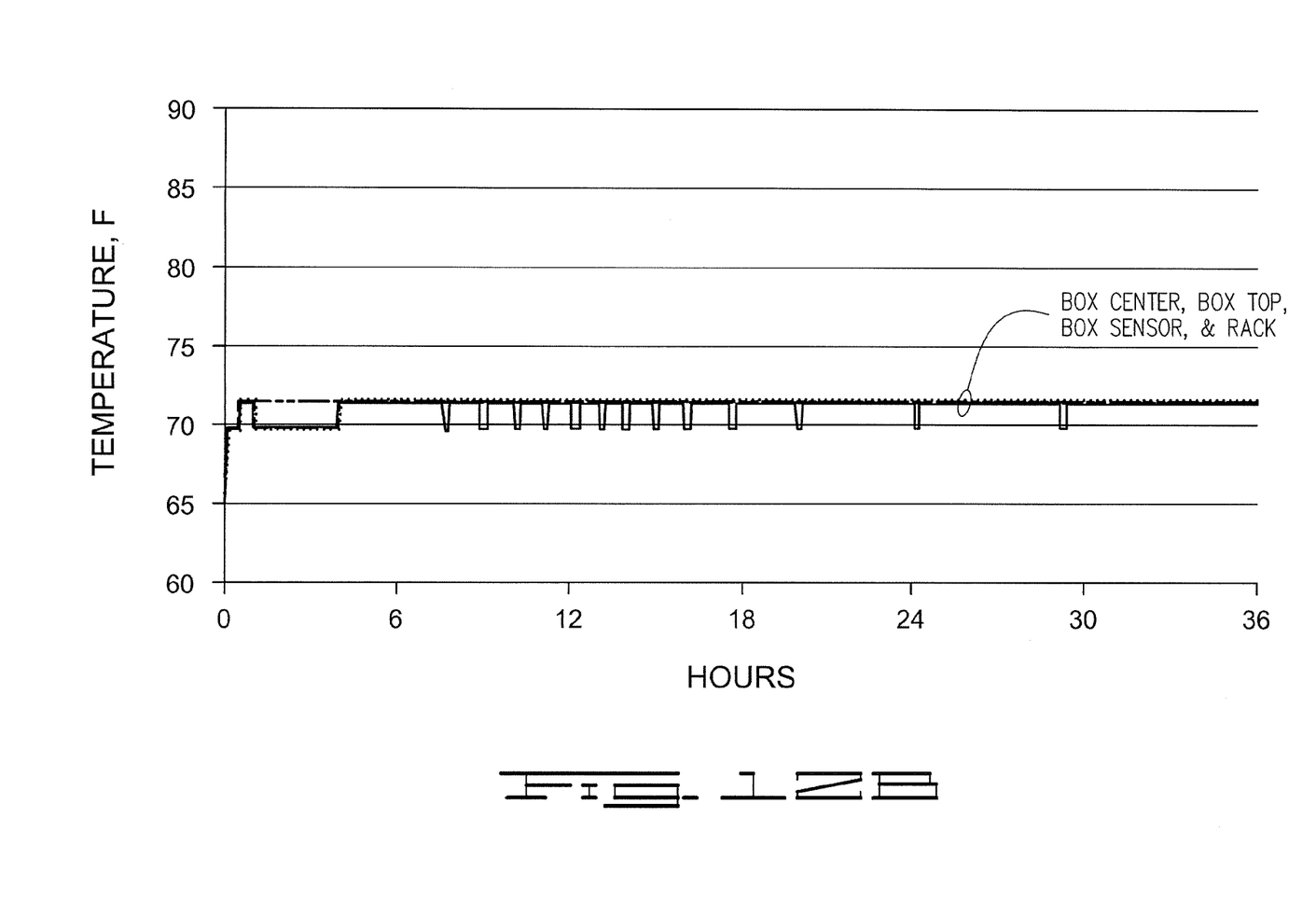
FIG. 12A is a graphic plot of variations in temperature measured at the top, at the center, at the rack, and at the temperature sensor of a prior art curing box.
FIG. 12B is a graphic plot of variations in temperature measured at the top, at the center, at the rack, and at the temperature sensor of a curing box constructed according to the present disclosure.
Figure 12A:
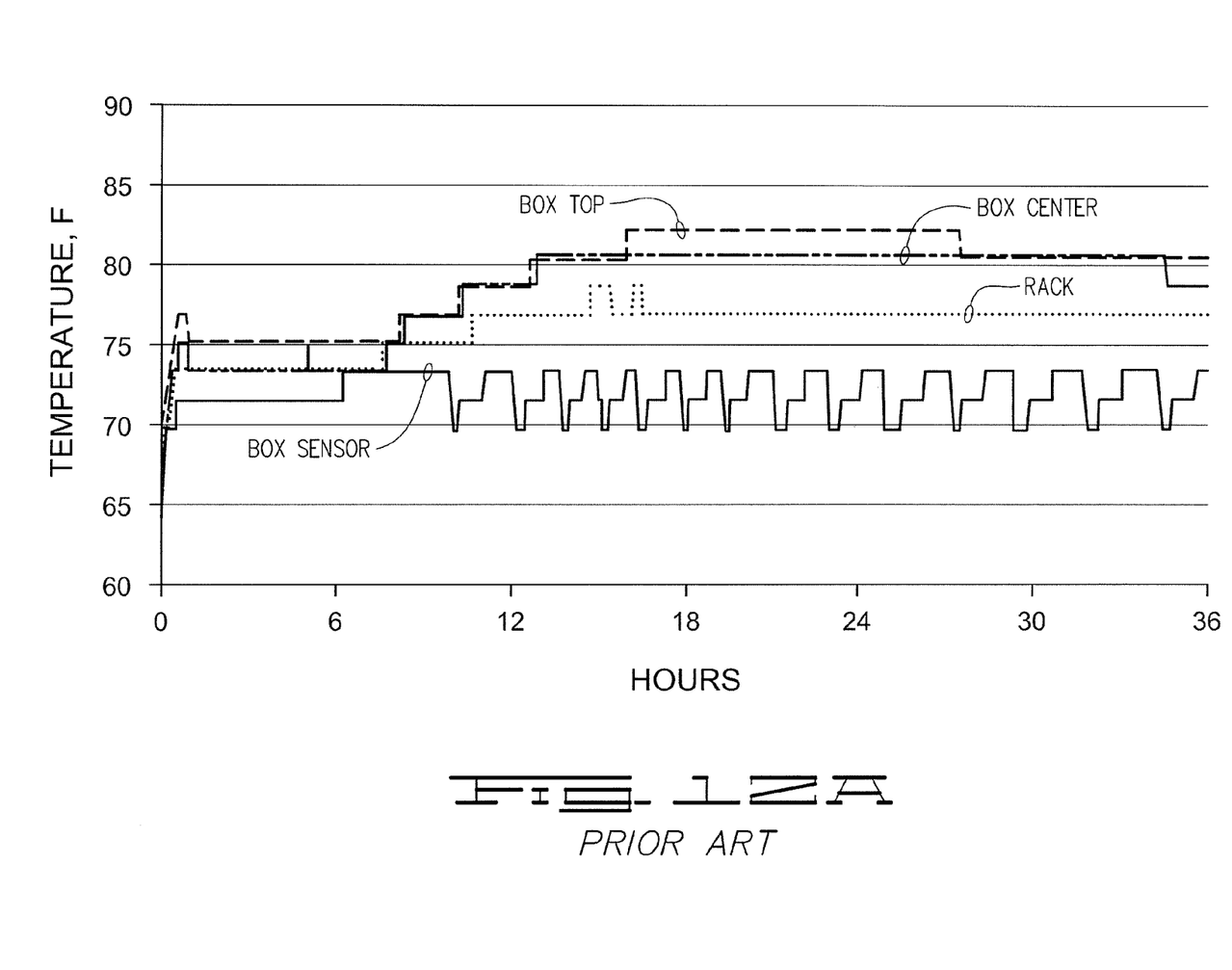

Reduction in temperature stratification is also shown in FIGS. 12A and 12B. FIG. 12A provides a graphical plot of temperature versus time including temperatures measured at the top, at the center, at the rack, and at the temperature sensor of a prior art curing box during curing. FIG. 12B provides a graphical plot of temperature versus time including temperatures measured at the top, at the center, at the rack, and at the sensor of the inventive curing box during curing. The temperature plots depicted in FIG. 12A show variations in the magnitude of the temperature measured each location, while the temperature plots of FIG. 12B are substantially similar in magnitude at each location. Thus, FIG. 12B demonstrates the ability of the inventive curing box to avoid temperature stratification.

From the above description, it is clear that the inventive concept(s) disclosed herein is well adapted to carry out the objects and to attain the advantages mentioned herein as well as those inherent in the inventive concept(s) disclosed herein. While presently preferred embodiments of the inventive concept(s) disclosed herein have been described for purposes of this disclosure, it will be understood that numerous changes may be made in the construction and the operation of the various components, elements and assemblies described herein, and/or in the steps or the sequence of steps of the methods described herein, which will readily suggest themselves to those skilled in the art and which are accomplished within the scope of the inventive concept(s) disclosed and claimed herein.

What is claimed is:

1. A curing box, comprising:
   a box containing a liquid;
   a fluid conduit positioned within the box, the fluid conduit in fluid communication with an exterior of the box and the fluid conduit carrying a plurality of emitters, wherein the emitters provide fluid communication between the fluid conduit and an interior of the box;
   wherein said emitters are arranged in at least one group on said fluid conduit, said group of emitters having at least two emitters and wherein at least two emitters in each group direct fluid flow in different directions; and,
   a fluid source, the fluid source in fluid communication with the fluid conduit, wherein the fluid source is configured to provide a volume of fluid under pressure to the fluid conduit;
   a heating element configured to adjust the temperature of the liquid in the box;
   a cooling element configured to adjust the temperature of the liquid in the box;
   a first sensor positioned to monitor the temperature of the liquid;
   a second sensor positioned external to the box to monitor a second temperature; and,
   a control module configured to receive and to record the temperature from the first sensor and to receive and to record the second temperature from the second sensor, wherein the control module is configured to control the activation and deactivation of the cooling element, and the activation and deactivation of the heating element to thereby adjust the temperature of the liquid to substantially correspond to the second temperature.

2. The curing box of claim 1, wherein the fluid source is positioned above a level of the liquid in the box.

3. The curing box of claim 1, wherein the fluid conduit has a length suitable to extend substantially from a first side of the box to a second side of the box, and wherein the fluid conduit carries at least three groups of emitters along the length of the fluid conduit.

4. The curing box of claim 1, wherein the fluid conduit has a length suitable to extend from a first side of the box to a second side of the box, and wherein the fluid conduit has at least three groups of emitters positioned equidistant from one another along the length of the fluid conduit.

5. The curing box of claim 1, wherein at least one emitter in at least one group of emitters is positioned on a bottom surface of the fluid conduit.

6. The curing box of claim 1, further comprising a rack positioned to support a specimen in the liquid contained in the box.

7. The curing box of claim 1, wherein the heating element, the cooling element, and the fluid conduit are positioned in a substantially coplanar arrangement with one another.

8. The curing box of claim 1, further comprising a transceiver configured to provide communication between the control module and a remote location.

9. The curing box of claim 1, wherein the fluid conduit has a length suitable to extend from a first side of the box to a second side of the box, and wherein the fluid conduit has at least three groups of emitters positioned equidistant from one another along the length of the fluid conduit and each group of emitters has at least three emitters and wherein at least two emitters in each group direct fluid flow in different directions.

10. The curing box of claim 3, wherein at least one emitter in at least one group of emitters is positioned on a bottom surface of the fluid conduit.

11. The curing box of claim 4, wherein at least one emitter in at least one group of emitters is positioned on a bottom surface of the fluid conduit.

12. The curing box of claim 1, further comprising a user input device said user input device replacing said second sensor, said control module configured to receive the temperature from the first sensor and to receive a preset temperature from the user input device, wherein the control module is configured to control the activation and deactivation of the cooling element, and the activation and deactivation of the heating element to thereby adjust the temperature of the liquid to substantially correspond to the preset temperature.

13. A method for curing a specimen, comprising:
   immersing the specimen in a first fluid in a curing box;
   providing a preset temperature for the first fluid in the curing box;
   monitoring the temperature of the first fluid;

heating or cooling the first fluid in the curing box to adjust the temperature of the first fluid to substantially correspond to the preset temperature;

providing a second fluid to the curing box; and distributing the second fluid through a plurality of emitters carried by a fluid conduit positioned within the curing box, wherein said emitters are arranged in at least one group having at least two emitters and wherein at least two emitters in each group direct fluid flow in different directions thereby circulating the first fluid throughout the curing box in a manner to preclude temperature stratification in the first fluid.

14. The method of claim 13, wherein at least one emitter directs the second fluid downward toward the bottom of the curing box.

15. The method of claim 13, wherein at least three groups of emitters distribute the second fluid, and wherein the groups of emitters are spaced substantially equidistant from one another in the curing box.

16. A method for curing a specimen, comprising:

immersing the specimen in a first fluid in a curing box;

monitoring the temperature of the first fluid in the curing box;

monitoring the temperature of a second specimen external to the curing box;

adjusting the temperature of the first fluid in response to the monitored temperature of the second specimen by heating or cooling the first fluid in the curing box;

providing a second fluid to the curing box; and distributing the second fluid through a plurality of emitters carried by a fluid conduit positioned within the curing box, wherein said emitters are arranged in at least one group having at least two emitters and wherein at least two emitters in each group direct fluid flow in different directions thereby circulating the first fluid throughout the curing box in a manner to preclude temperature stratification in the first fluid.

17. The method of claim 16, wherein at least one emitter directs the second fluid downward toward the bottom of the curing box.

18. The method of claim 16, wherein at least three groups of emitters distribute the second fluid, and wherein the groups of emitters are spaced substantially equidistant from one another in the curing box.

19. The method of claim 16, wherein the step of adjusting the temperature of the first fluid adjusts the temperature of the first fluid to substantially correspond to the temperature of the second specimen.

* * * * *